United States Patent
Heimann et al.

(10) Patent No.: US 9,452,196 B2
(45) Date of Patent: Sep. 27, 2016

(54) PHARMACEUTICAL COMPOSITION FOR TREATING MEDICAL CONDITIONS AND A METHOD FOR TREATING ALIMENTARY DISORDERS AND RELATED DISEASES

(71) Applicant: SOCIEDADE BENEFICENTE DE SENHORAS HOSPITAL SIRIO LIBANES, São Paulo-SP (BR)

(72) Inventors: Andrea Sterman Heimann, Cotia (BR); Camila Squarzoni Dale, São Paulo (BR); Lakshmi A. Devi, New Rochelle, NY (US)

(73) Assignee: Sociedade Beneficente de Senhoras Hospital Sirio Libanes, Sao Paulo (BR)

( * ) Notice: Subject to any disclaimer, the term of this patent is extended or adjusted under 35 U.S.C. 154(b) by 0 days.

(21) Appl. No.: 14/703,466

(22) Filed: May 4, 2015

(65) Prior Publication Data

US 2015/0297669 A1   Oct. 22, 2015

Related U.S. Application Data

(63) Continuation of application No. 13/388,194, filed as application No. PCT/BR2010/000253 on Jul. 30, 2010, now abandoned.

(30) Foreign Application Priority Data

Jul. 31, 2009 (BR) ..................................... 0902481

(51) Int. Cl.

| | | |
|---|---|---|
| *A61K 38/00* | (2006.01) | |
| *A61P 3/04* | (2006.01) | |
| *A61K 38/08* | (2006.01) | |
| *A61K 38/42* | (2006.01) | |
| *A61K 45/06* | (2006.01) | |
| *C07K 7/06* | (2006.01) | |

(52) U.S. Cl.
CPC .............. *A61K 38/08* (2013.01); *A61K 38/42* (2013.01); *A61K 45/06* (2013.01); *C07K 7/06* (2013.01)

(58) Field of Classification Search
CPC ................................. A61K 38/08; C07K 7/06
See application file for complete search history.

(56) References Cited

U.S. PATENT DOCUMENTS

| 7,169,754 B2 | 1/2007 | Papadimitriou |
| 2005/0101542 A1 | 5/2005 | Piomelli et al. |
| 2006/0100205 A1 | 5/2006 | Weber et al. |

FOREIGN PATENT DOCUMENTS

| BR | 2001 14410 A | 2/2004 |
| WO | WO 2006/100205 A2 | 9/2006 |
| WO | WO 2006/119260 A2 | 11/2006 |

OTHER PUBLICATIONS

International Search Report and Written Opinion from International Application No. PCT/BR2010/000253, filed Jul. 30, 2010.
Van Gaal L F et al.: "Effects of the cannabinoid-1 receptor blocker rimonabant on weight reduction and cardiovascular risk factors in overweight patients: 1-year experience from the RIO-Europe study", Lancet; vol. 365, Apr. 16, 2005; pp. 1389-1397, XP002614949.
Oldfield B J et al: "The effect of the cannabinoid receptor antagonist, rimonabant (SR 141716) on energy expenditure"; Appetite, Academic Press, New York, NY, US; vol. 49; No. 1; May 17, 2007; p. 337; XP022083436.
Heimann A S et al: "Hemopressin is an inverse agonist of CB1 cannabinoid receptors", PNAS; vol. 104; No. 51; Dec. 18, 2007; pp. 20588-20593; XP002614960.
Witkin et al: "A therapeutic role for cannabinoid CB1 receptor antagonists in major depressive disorders"; Trends in Pharmacological Sciences, Elsevier, Hayworth, GB; vol. 26; No. 12; Dec. 1, 2005; pp. 609-617; XP005168624.
Dodd G T et al: "The peptide homopressin acts through CB1 cannabinoid receptors to reduce food intake in rats and mice"; The Journal of Neuroscience; vol. 30, No. 2; May 26, 2010; pp. 7369-7376; XP002614943.
Rioli et al., *The Journal of Biological Chemistry*, 2003, vol. 278, No. 10, pp. 8547-8555.
Zhang et al., *Diabetes*, Jun. 2007, vol. 56, 1647-1654.
International Preliminary Report on Patentability for Application No. PCT/BR2010/000253 dated Jan. 17, 2012.
Boden, G., *Free Fatty Acids, a Link Between Obesity and Insulin Resistance*, 3 Front. Biosci. 169-175 (1998).
Christensen, R. et al., *Efficacy and Safety of the Weight-Loss Drug Rimonabant*, 370 Lancet 1706-1713 (2007).
Dale, C. S. et al., *Antinociceptive Action of Hemopressin in Experimental Hyperalgesia*, 25 Peptides 431-436 (2005).

*Primary Examiner* — James H Alstrum Acevedo
*Assistant Examiner* — Kaipeen Yang
(74) *Attorney, Agent, or Firm* — Alston & Bird LLP

(57) ABSTRACT

The present invention refers to a pharmaceutical composition that includes an active ingredient, such as a peptide, which acts as an antagonist and/or inverse agonist of a G protein-coupled receptor and pharmaceutically acceptable vehicle. The pharmaceutical composition may be used for the treatment of obesity and the prevention of and the treatment of diabetes.

12 Claims, 7 Drawing Sheets

Figure 1A:
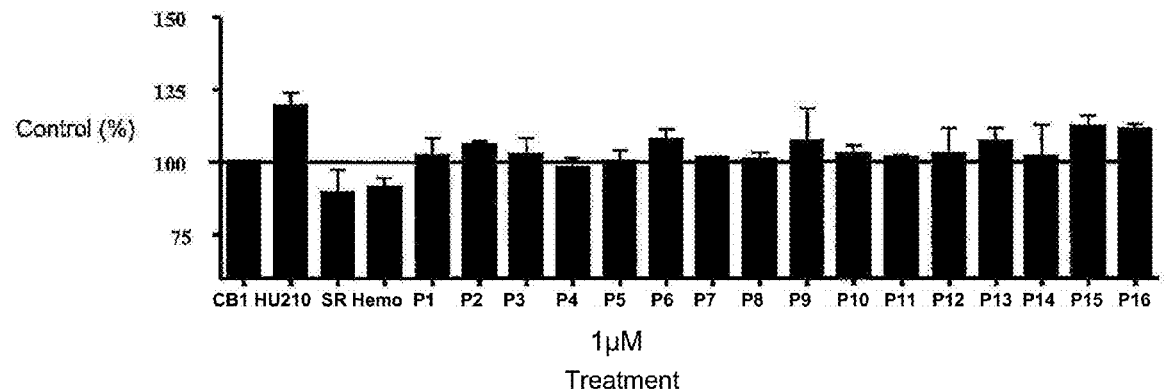

PHARMACEUTICAL COMPOSITION FOR TREATING MEDICAL CONDITIONS AND A METHOD FOR TREATING ALIMENTARY DISORDERS AND RELATED DISEASES

CROSS-REFERENCE TO RELATED APPLICATIONS

This application is a continuation of U.S. application Ser. No. 13/388,194, filed Jan. 31, 2012, which is a national phase entry of International Application No. PCT/BR2010/000253, filed Jul. 30, 2010, which claims priority to Brazilian Application No. PI0902481-6, filed Jul. 31, 2009, which are hereby incorporated herein in their entirety by reference.

FIELD

The present invention refers to a pharmaceutical composition, which comprises an active ingredient acting as an antagonist or inverse agonist of a G protein-coupled receptor and a pharmaceutically acceptable vehicle. Said pharmaceutical composition may be used for the treatment of obesity. Said pharmaceutical composition may also be used for the treatment of diabetes.

BACKGROUND

Guanine nucleotide-binding proteins, otherwise known as G proteins, are involved in transmitting chemical signals from outside the cell to inside the cell by way of triggering a series of biochemical reactions which ultimately effect physiological changes within the cell. G protein-coupled receptors are transmembrane receptors that sense molecules outside the cell and activate signal transduction pathways and intracellular responses. It is well known that G protein-coupled receptors are involved in regulating many diseases.

Type 1 and type 2 cannabinoid receptors, hereinafter $CB_1$ and $CB_2$, are G protein-coupled receptors found in mammal tissues. $CB_1$ receptors are expressed mainly by neurons of the central and peripheral nervous system, whereas the $CB_2$ receptors occur centrally and peripherally particularly in immune cells. Signal molecules may bind to the two cannabinoid receptors outside the cell, causing a cascade of biochemical reactions within the cell. For example, $CB_1$ receptors coupled through G proteins inhibit adenylyl cyclase and activate mitogen-activated protein (MAP) kinase. In addition, $CB_1$ receptors inhibit presynaptic N- and P/Q-type calcium channels and activate inwardly rectifying potassium channels. The combined effect of these biochemical changes generates a variety of physiological effects, of which many are still to be discovered.

The discovery that mammal tissues express cannabinoid receptors was accompanied by the discovery of endogenous ligands to these receptors called endocannabinoids, which along with $CB_1$ and $CB_2$ constitute the endocannabinoid system. It was discovered that certain disorders cause the levels of endocannabinoids, the density of the cannabinoid receptors and the efficiency of the coupling of the cannabinoid receptors to increase. It has been noted that this upregulation of the endocannabinoid system often suppresses undesirable symptoms and signals, suggesting that the endocannabinoid system is autoregulatory.

In order to better understand the endocannabinoid system, researchers have been developing antagonists and inverse agonists with specificity for either $CB_1$ or $CB_2$. Antagonists are receptor ligands that do not provoke a biological response upon binding to a receptor but block or weaken an agonist-mediated response. Inverse agonists on the other hand bind to the same receptor as an agonist and reverse the activity of receptors, or in other words, exert an opposite pharmacological effect of a receptor agonist.

The discovery of antagonists and inverse agonists of $CB_1$ or $CB_2$ receptors is extremely important in the field of medicine as there are many significant physiological and pathophysiological conditions in which the endocannabinoid system has been demonstrated to play a role. These include diseases of the central nervous system such as Parkinson's, Alzheimer's, and depression, as well as diseases of the peripheral nervous system, such as inflammatory and neuropathic pain, obesity and other alimentary disorders.

Incidentally, there are several published accounts documenting the importance of antagonists or inverse agonists of either $CB_1$ or $CB_2$ receptors in the prophylactic or combative treatment of the aforementioned diseases. For example, WO/2006/119260 refers to a pharmaceutical composition of an antagonist of the $CB_1$ receptor in association with a microsomal triglyceride transfer protein inhibitor which acts in the intestine to treat obesity or alimentary disorders. WO/2006/100205 refers to new cannabinoid receptor modulators and their use to treat diseases such as pain, neurodegenerative disorders and alimentary disorders. US/2005/101542 refers to yet another pharmaceutical composition comprising cannabinoid receptor antagonists that combined with another protein agonist can reduce the consumption of foods, alcohol, or other appetizing substances. Finally, Brazilian patent application PI0114410-3 refers to the pharmaceutical combination of the antagonist of $CB_1$ and the appetite suppressant sibutramine that is useful in the treatment of obesity.

One underlying feature of these published accounts is that they demonstrate how an antagonist or inverse agonist of $CB_1$ may treat obesity. $CB_1$ receptors are targets for treating obesity because they are highly expressed in hypothalamic areas which are involved in central food intake control and feeding behavior. These regions are also interconnected with the mesolimbic dopamine pathway, the so-called "reward" system. Furthermore, peripheral $CB_1$ receptors are located in the gastrointestinal tract, liver and in adipose tissue. These combined facts strongly indicate that the endocannabinoid system may be directly involved in feeding regulation, fat control and blood glucose regulation. For example, it is known in the literature that the administration of exogenous $CB_1$ agonists such as $\Delta^9$-tetrahydrocannabinol (THC), the active ingredient of Cannabis sativa, increases food intake by increasing motivational rewards. Antagonism of $CB_1$ could potentially inverse these effects by inhibiting the dopamine-mediated rewarding properties of food and by inversing the process for storage of fats.

Obesity is now the most common nutritional disorder in industrialized countries. Defined as a body mass index of greater than 30, obesity arises from the accumulation of excess fat in the body from over consumption of fatty foods. Prevalence of obesity in the US and Europe has reached epidemic levels. Data from the World Health Organization Multinational MONICA (MONitoring of trends and determinants in CArdiovascular diseases) project shows that in some parts of Europe over 70% of men aged 55-64 years are clinically obese or overweight and almost 70% of women in this age group. Furthermore, one in five of all Americans are obese and one in three overweight. In addition, increasing rates of childhood obesity are likely to exacerbate the trend towards increasing obesity in adulthood.

In addition, research indicates that obese individuals are predisposed to insulin resistance and diabetes. (see Boden, *Free fatty acids, a link between obesity and insulin resistance,* 3 Front. Biosci. 169-75 (1998)). Insulin resistance is a term referring to the condition when one's cells have become less sensitive to the effects of insulin in balancing blood glucose levels. Insulin is the hormone secreted by the pancreas which helps glucose to enter cells where it is turned into energy. Obese individuals have high levels of free fatty acids in their blood plasma. Free fatty acids lead to increased insulin resistance because they compete with and inhibit insulin from stimulating glucose uptake, thus leading to increased and potentially life threatening blood glucose levels. Hence, decreasing the amount of free fatty acids and increasing insulin sensitivity is central to the prevention and treatment of diabetes.

People that experience insulin resistance provoke the pancreas to work harder and release increasing amounts of insulin to achieve a healthy blood glucose balance. This can lead to two major problems. First, the pancreas may become exhausted and insulin production may therefore slow down to abnormally low levels. This would trigger adult onset type II diabetes by increasing blood glucose levels. A second potential problem may be that the insulin resistant patient does not develop diabetes but may suffer from abnormally high levels of insulin in the blood which can cause chronic obesity, high blood pressure, heart disease and possibly some cancers.

There are no prior art documents suggesting a pharmaceutical composition of hemopressin, a mimic, derivative or fragment thereof to treat diabetes.

A synthetic compound, rimonabant (SR141716A), has however been demonstrated to behave as an inverse agonist at the $CB_1$ receptor and achieve weight-reducing effects over extended periods in rodents and humans (see Van Gaal et al., *Effects of the cannabinoid-1 receptor blocker rimonabant on weight reduction and cardiovascular risk factors in overweight patients,* 365 Lancet 1389-1397 (2005)). The action of rimonabant is limited however as the United States Food and Drug Administration rejected rimonabant because clinical trials suggested a higher incidence of depression, anxiety, and suicidality following prolonged administration (see R. Christensen et al., *Efficacy and safety of the weight-loss drug rimonabant,* 370 Lancet 1706-1713 (2007)). Current research efforts are therefore underway to find safer compounds that behave as selective antagonists or inverse agonists of the $CB_1$ receptor.

The peptide hemopressin may be a safer alternative compound that exhibits selectivity for $CB_1$. Hemopressin is a product of the hemoglobin a chain, discovered in rat brain homogenates. Further studies have indicated that peptides containing the hemopressin amino acid sequence are generated in vivo, suggesting indeed that hemopressin may be a safer alternative than rimonabant or other synthetic inverse agonists or antagonists of $CB_1$, because of its potential endogenous presence.

Hemopressin was initially found by Dale et al. to have nonopioid antinociceptive effects (see *Antinociceptive action of hemopressin in experimental hyperalgesia,* 25 Peptides 431-436 (2005)). Further studies demonstrated that the peptide hemopressin acts specifically on the cannabinoid system as a $CB_1$ receptor inverse agonist and can interact with both peripheral and central pain pathways in vivo (see Heimann et al., *Hemopressin is an inverse agonist of $CB_1$ cannabinoid receptors,* 104 PNAS 20588-593 (2007)). This article also demonstrated how hemopressin is effective in treating hyperalgesia when administered locally or systemically. Furthermore, this article suggested that based on hemopressin's specificity for $CB_1$ it may have an effect on body weight and food intake in the same way as rimonabant.

A recent article, published in the Journal of Neuroscience on May 26, 2010 by Garron T. Dodd et al., titled *The peptide hemopressin acts through $CB_1$ cannabinoid receptors to reduce food intake in rats and mice,* demonstrates how hemopressin acts as an inverse agonist on $CB_1$ receptors and modulates the activity of appetite pathways in the brain in a manner contrary to how THC, and other $CB_1$ agonists, modulate appetite pathways in the brain. More specifically, Dodd shows that hemopressin can: 1) antagonize $CB_1$ agonist-induced internalization of the $CB_1$ receptor in vitro; 2) induce hypophagia in vivo when administered centrally; 3) induce hypophagia in vivo when administered systemically; 4) overcome powerful orexigenic drives in fasted or obese mice; and 5) reduce feeding in a behaviorally specific manner.

SUMMARY

In light of the increasing public health concerns regarding obesity and diabetes, many researchers throughout the world have attempted to find a pharmaceutical composition that can be used for the treatment of obesity and diabetes.

The objective of this invention is to present a pharmaceutical composition for the treatment of obesity, without causing depression, by oxidizing free fatty acids in blood plasma. This invention also suggests a pharmaceutical composition for the prevention and treatment of diabetes by increasing insulin sensitivity.

The objective of the present invention is achieved by a pharmaceutical composition comprising an active ingredient, including a mimic, derivative or fragment thereof, which may act as an inverse agonist or antagonist of G protein-coupled receptors, particularly $CB_1$, and a pharmaceutically acceptable vehicle.

The present invention refers to a pharmaceutical composition, which comprises an active ingredient, a mimic, derivative or fragment thereof, behaving as an inverse agonist and/or antagonist of a G protein-coupled receptor and a pharmaceutically acceptable vehicle. The G protein-coupled receptor targeted in this invention is a cannabinoid receptor and in particular the $CB_1$ receptor. Preferably, said active ingredient is the peptide hemopressin, with the following amino acid sequence PVNFKFLSH (proline-valine-asparagine-phenylalanine-lysine-phenylalanine-leucine-serine-histidine) (SEQ ID NO:8), or a mimic, derivative or fragment thereof. The pharmaceutically acceptable vehicle is preferably a sterile isosmotic solution with the same osmotic pressure of an isotonic solution of blood and that is compatible with the active ingredient.

The invention describes how said pharmaceutical composition may be used in the treatment of obesity by reducing fat content without causing any symptoms of depression by oxidizing fatty acids in blood plasma in muscles and the liver. The invention also reveals how said pharmaceutical composition may be used in the prevention and treatment of diabetes by increasing insulin sensitivity and thereby decreasing insulin resistance. Furthermore, this invention demonstrates that said pharmaceutical composition can effectively achieve said results through any of the following administrative routes: oral, intraperitoneal, or intrathecal.

The prior art suggests that administration of hemopressin could decrease food intake in normal and obese mice, whether administered systemically or locally. The present invention however demonstrates that local or systemic administration of a pharmaceutical composition of hemopressin, a mimic, derivative, or fragment thereof, will directly decrease fat content and body weight, without any symptoms of depression, by oxidizing fatty acids in blood plasma in muscles and the liver.

The state of the art therefore contains no mention or suggestion of the specific use of hemopressin, or a mimic, derivative, or fragment thereof, as part of a pharmaceutical composition which can be used in the preventative or combative treatment of obesity by reducing fat content and body weight without causing any symptoms of depression by oxidizing fatty acids in the blood plasma in muscles and the liver. The state of the art also does not teach how a pharmaceutical composition of hemopressin, its mimics, derivatives or fragments thereof, can prevent and treat diabetes by increasing insulin sensitivity, lowering insulin resistance and thereby balancing blood glucose levels.

Experiments were conducted on genetically obese and a diet-induced obesity models demonstrating that a pharmaceutical composition containing hemopressin, a mimic, derivative or fragment thereof, can effectively reduce fat content and body weight in rats after either intraperitoneal or oral administration by acting as inverse agonists or as antagonists of the $CB_1$ receptor. Experiments to measure symptoms of depression were performed and rats treated with a pharmaceutical composition of hemopressin, mimics, derivatives, or fragments thereof exhibited normal behavior in a standardized stress test.

Additionally, a pharmaceutical composition of hemopressin, a mimic, derivative, or fragment thereof, may be administered for the prevention and treatment of diabetes by increasing insulin sensitivity and thereby decreasing insulin resistance and effectively ameliorating dangerously high blood glucose levels. The biochemical process affected by inverse agonistic or antagonistic binding to $CB_1$ triggers increased oxidation of fatty acids in blood plasma in muscles and the liver, decreasing the amount of free fatty acids and thus decreasing insulin resistance. As aforementioned, free fatty acids compete with and inhibit insulin from stimulating glucose uptake, thus leading to increased and potentially life threatening blood glucose levels. Hence, decreasing the amount of free fatty acids and increasing insulin sensitivity is central to the prevention and treatment of diabetes.

A pharmaceutical composition for the treatment of obesity comprising an active ingredient, a mimic, derivative, or fragment thereof, which acts as an antagonist or inverse agonist of cannabinoid type 1 receptor and a pharmaceutically acceptable vehicle, characterized by the fact that administration of said pharmaceutical composition reduces body fat content by oxidizing free fatty acids in blood plasma.

A pharmaceutical composition comprising an active ingredient, a mimic, derivative, or fragment thereof, which acts as an antagonist or inverse agonist of cannabinoid type 1 receptors and a pharmaceutically acceptable vehicle, characterized by the fact that administration of said pharmaceutical composition improves prevents and treats diabetes by means of oxidizing free fatty acids in blood plasma.

SUMMARY DESCRIPTION OF THE FIGURES

Figure 1B:
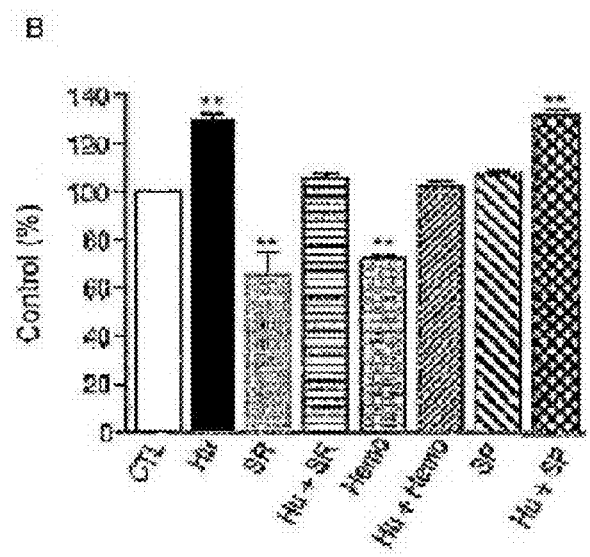
Figure 2A:
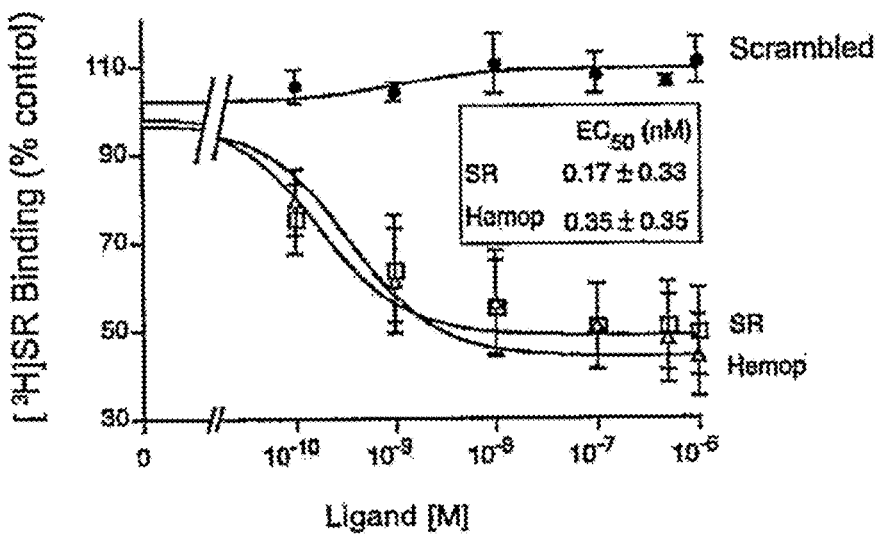
Figure 2B:
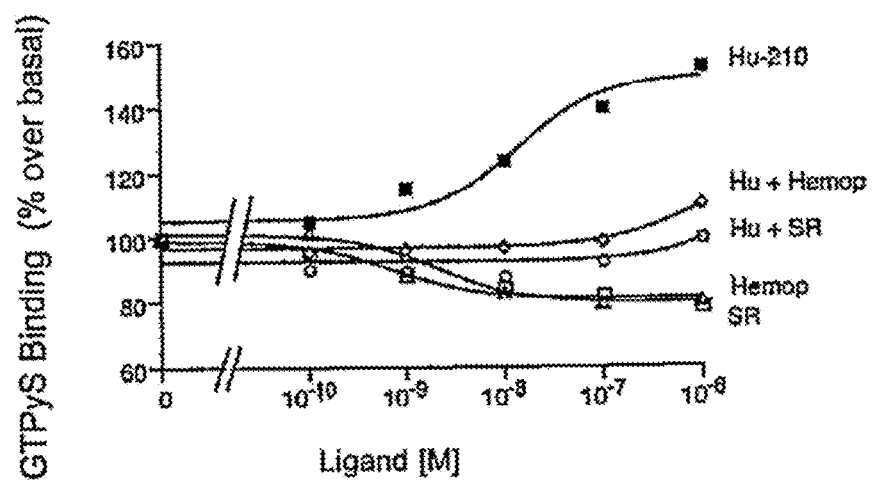
Figure 2C:
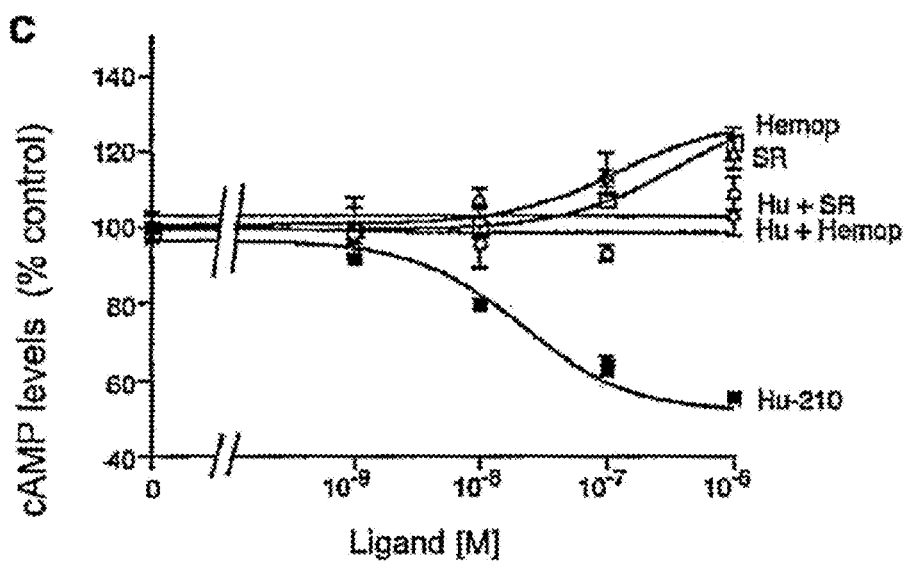
Figure 2D:
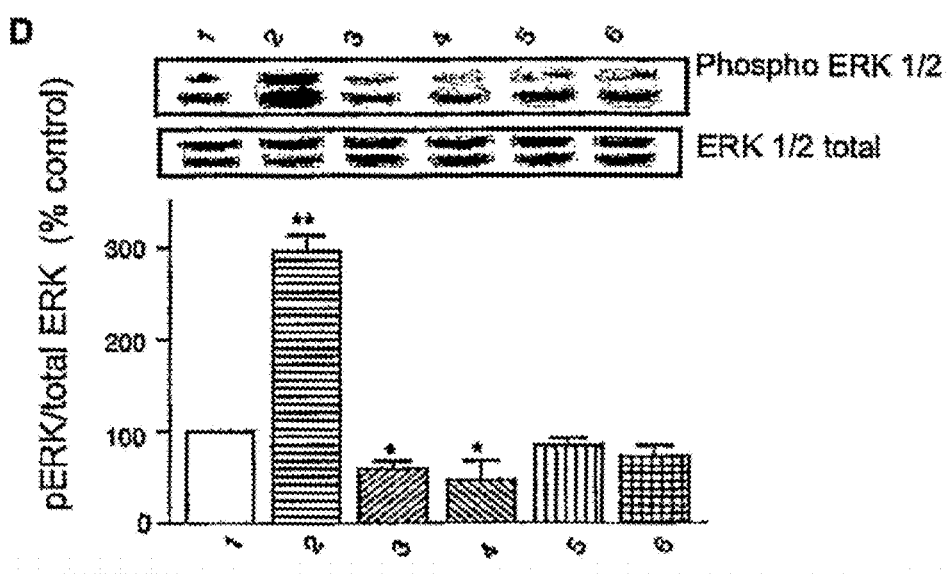
Figure 3A:
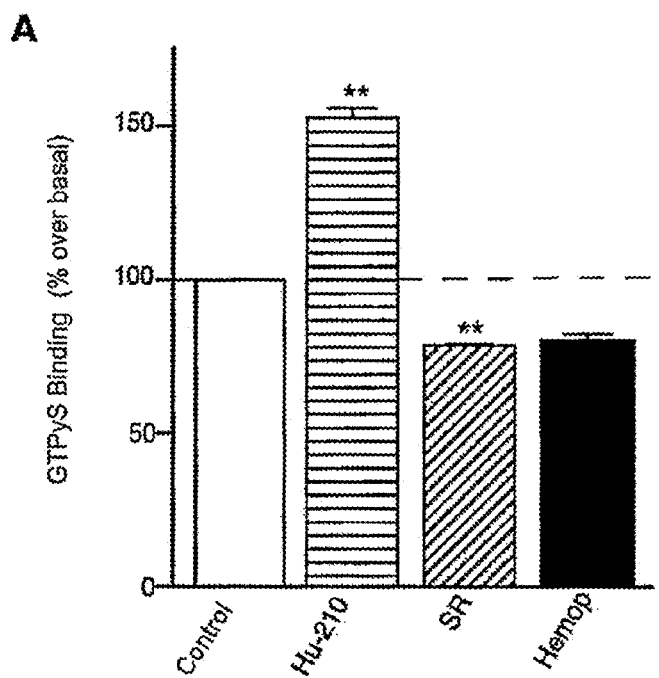
Figure 3B:
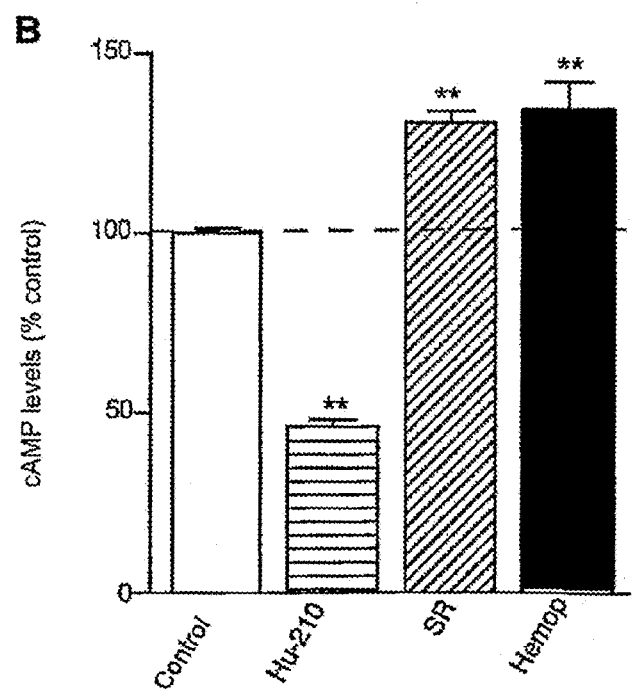
Figure 3C:
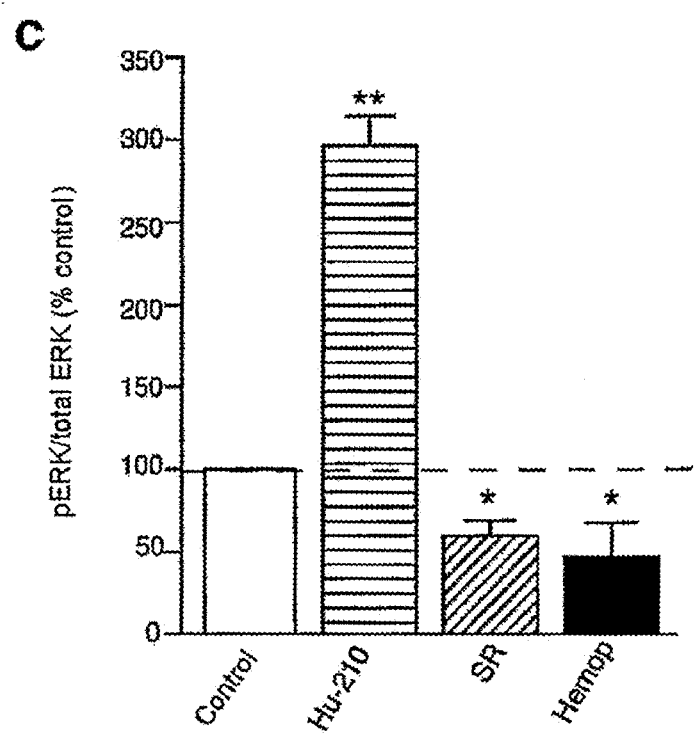
Figure 3D:
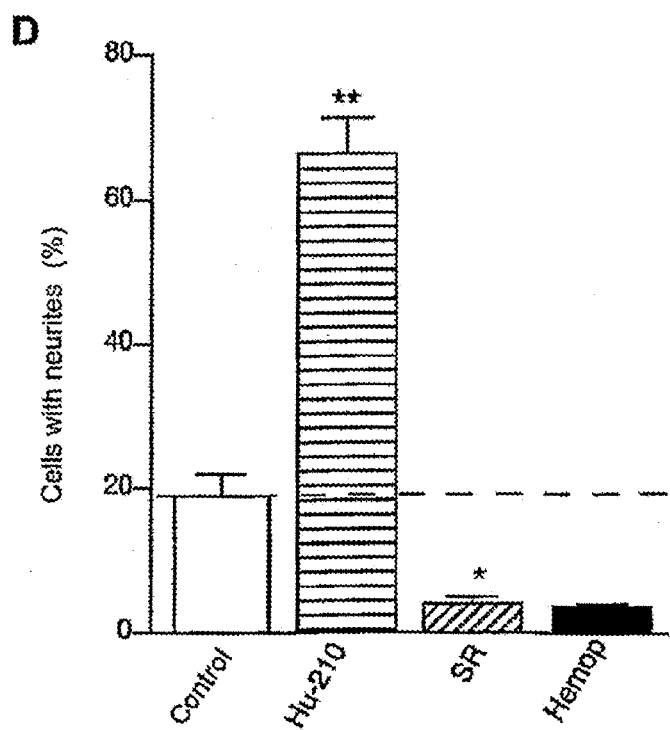
Figure 4A:
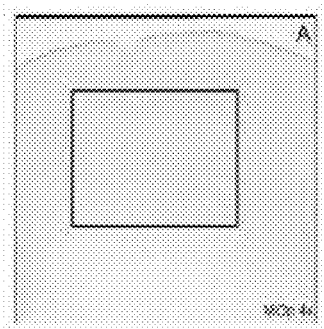
Figure 4B:
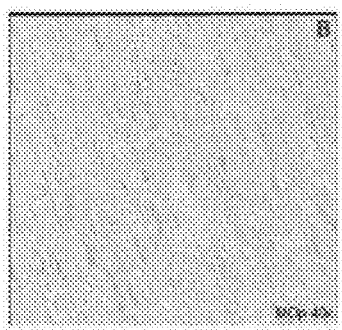
Figure 4C:
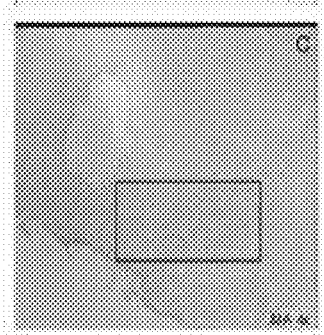
Figure 4D:
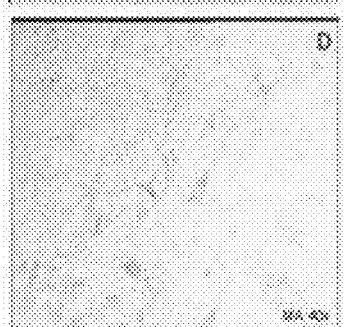
Figure 4E:
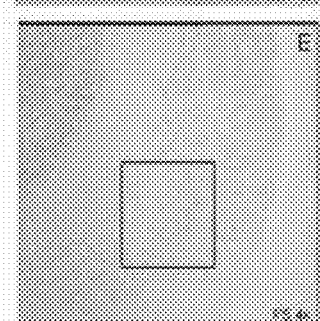
Figure 4F:
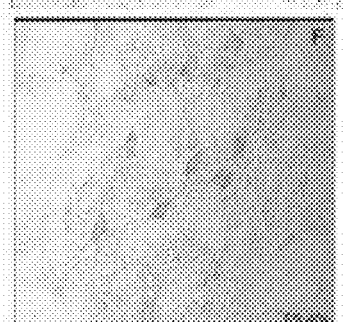
Figure 4G:
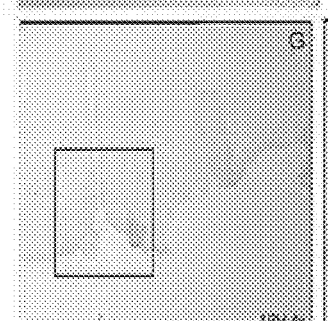
Figure 4I:
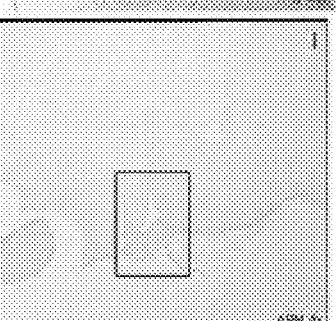
Figure 4H:
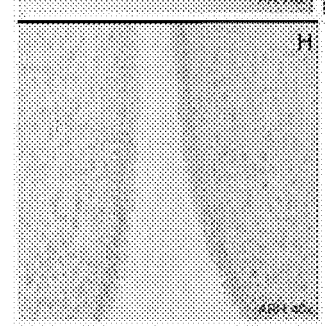
Figure 4J:
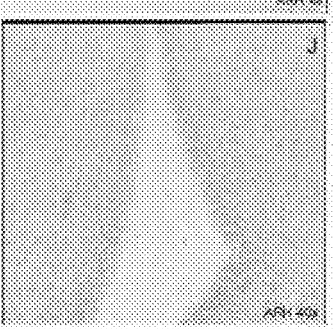
Figure 5:
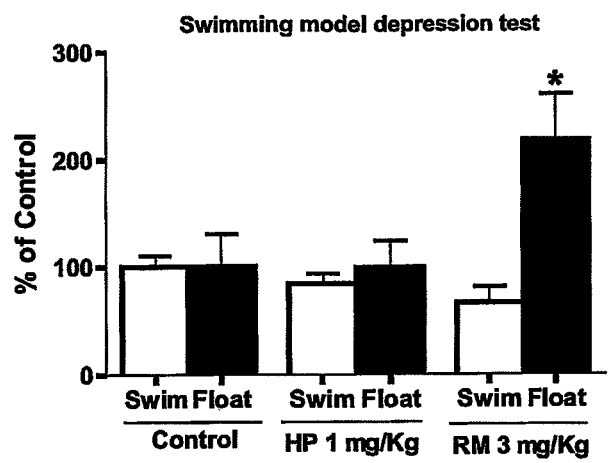
Figure 6:
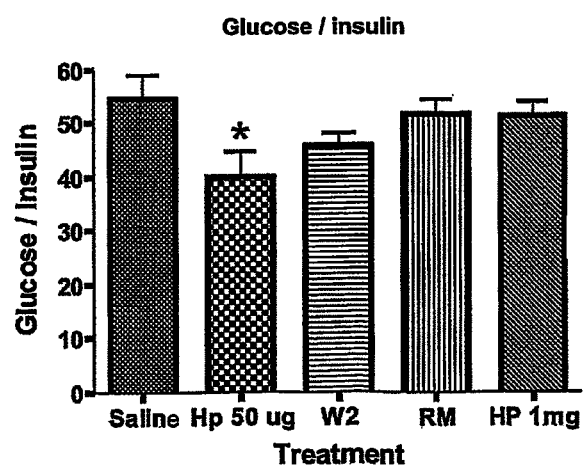

Reference is next made to the appended figures for an improved understanding of the more detailed description of the invention that follows:

FIG. 1A—identifies hemopressin as a peptide modulator of $CB_1$ receptor;

FIG. 1B—illustrates that hemopressin behaves similarly to rimonabant;

FIG. 2A—illustrates that hemopressin is capable of displacing the high-affinity ligand rimonabant from $CB_1$ receptor;

FIG. 2B—illustrates that hemopressin is capable of blocking the increase in GTPgammaS, as measured against the agonist HU-210;

FIG. 2C—illustrates that hemopressin is capable of preventing decreases in cAMP levels, as measured against the agonist HU-210;

FIG. 2D—illustrates that hemopressin is capable of blocking phosphorylation of ERK1 and ERK2, as measured against the agonist HU-210;

FIG. 3A—illustrates that hemopressin acts as an inverse agonist of $CB_1$ receptors by causing decreases in signaling as measured by binding to GTPgammaS ligand;

FIG. 3B—illustrates that hemopressin acts as an inverse agonist of $CB_1$ receptors by causing decreases in signaling as measured by adenylate cyclase catalyst activity;

FIG. 3C—illustrates that hemopressin acts as an inverse agonist of $CB_1$ receptors by causing decreases in signaling as measured by MAP kinase phopshorylation;

FIG. 3D—illustrates that hemopressin efficiently blocks the growth of neurites in neural 2A cells as measured against agonists;

FIGS. 4A-J—illustrate the immunohistochemistry in the brain of rats demonstrating that hemopressin is a naturally occurring peptide in vivo;

FIG. 5—illustrates that treatment with hemopressin does not cause depression in rats as compared to treatment with rimonabant;

FIG. 6—illustrates how treatment of hemopressin on diet-induced obesity models improves insulin sensitivty.

DETAILED DESCRIPTION

The pharmaceutical composition herein claimed is useful for the treatment of obesity and for the prevention and treatment of diabetes.

The present invention demonstrates that hemopressin, an alpha hemoglobin fragment originally identified in extracts of rat brain using an enzyme capture technique and defined by the amino acid sequence PVNFKFLSH (proline-valine-asparagine-phenylalanine-lysine-phenylalanine-leucine-serine-histidine) (SEQ ID NO:8), is a peptide inverse agonist of $CB_1$ receptors. The molecular structure of hemopressin is illustrated below:

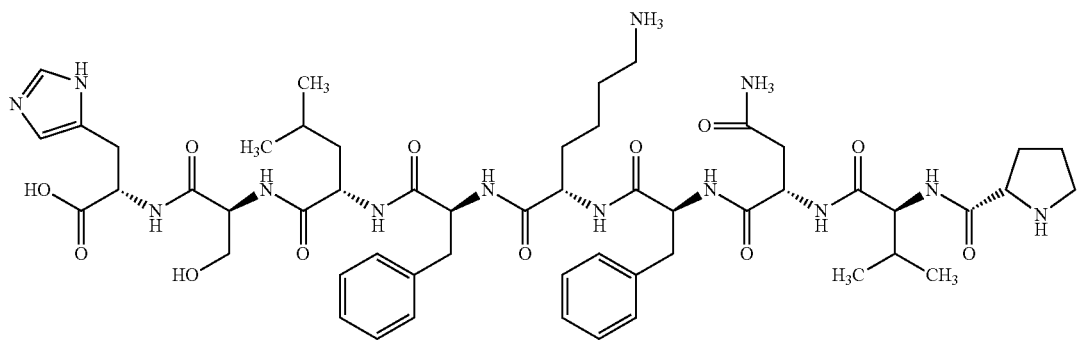

The identification of hemopressin as peptide modulator of $CB_1$ receptor can be seen in FIG. 1A, where it was discovered that among all the peptides tested only hemopressin was able to decrease the recognition of a $CB_1$ specific antibody. The study shown in FIG. 1B shows that the increase induced by the $CB_1$ agonist HU-210 in the recognition of the antibody can be significantly blocked both by hemopressin and by rimonanbant, suggesting that hemopressin behaves similarly to rimonanbant.

Next the selectivity of hemopressin for $CB_1$ receptors was examined using antibodies sensitive to the conformations of mu and delta opiod receptors, alpha-2A and beta-2 adrenergic receptors, as well as type 1 and 2 Angiotensin II receptors. In the following table, it is possible to identify the specificity of the peptide hemopressin for the $CB_1$ receptor. Hemopressin acts only on the $CB_1$ receptor, so it appears that hemopressin is highly selective for $CB_1$ receptors. The following data presents the percentage of activity as compared to the control group:

|  | Agonist | Hemopressin (HP) | Agonist and HP |
| --- | --- | --- | --- |
| $CB_1$ | 130.02 ± 5.91 | 72.30 ± 3.32 | 102.06 ± 5.91 |
| mu opioid | 140.09 ± 6.01 | 105.62 ± 1.09 | 141.09 ± 6.46 |
| delta opioid | 133.99 ± 10.16 | 100.65 ± 4.29 | 131.08 ± 3.35 |
| alpha-2A | 125.43 ± 7.34 | 102.72 ± 2.00 | 130.05 ± 7.06 |
| beta-2 | 150.44 ± 3.35 | 103.85 ± 9.29 | 157.40 ± 8.15 |
| AT1 | 143.01 ± 4.26 | 109.65 ± 1.31 | 140.01 ± 1.21 |
| AT2 | 134.01 ± 2.17 | 99.65 ± 4.71 | 137.10 ± 1.91 |

Given these results it was examined whether hemopressin managed to displace the highly affinitive ligand rimonabant from $CB_1$ receptors. As can be seen in FIG. 2A, hemopressin is capable of displacing rimonabant from $CB_1$ receptors. A test was then designed, the results of which are illustrated in FIG. 2B, to determine if hemopressin could block the signaling of $CB_1$ receptor. It was discovered that hemopressin is capable of blocking the increase of GTPgammaS as measured against the $CB_1$ receptor agonist HU-210. Hemopressin was also discovered to block decreases in cAMP levels with efficiency similar to that of rimonabant as measured against agonists as can be seen in FIG. 2C. Finally, a test was designed to measure whether hemopressin is capable of blocking the increase of levels of phosphorylated ERK1 and ERK2. Hemopressin, was found to behave similarly to rimonabant in this test as well, as illustrated in FIG. 2D. The combined analysis of FIGS. 2A-2D demonstrates that hemopressin binds to $CB_1$ receptors and behaves similarly to the highly selective, synthetic $CB_1$ receptor antagonist rimonabant.

Hemopressin was also determined to not only act as an antagonist but as an inverse agonist of $CB_1$ receptors. This was further explored by studying the binding of GTPgammaS, adenylate cyclase activity and MAP kinase phopshorylation. In all cases, it was possible to observe that hemopressin, similar to rimonabant, causes decreases in signaling below the basal levels. This can clearly be seen in FIGS. 3A-C. In addition, the activation of $CB_1$ receptors, particularly by $CB_1$ agonist HU-210, leads to induction of the growth of neurites in 2A neural cells. It was discovered that, like rimonabant, hemopressin efficiently blocks the growth of neurites as measured against agonists in 2A neural cells and that hemopressin alone is capable of decreasing the basal growth of neurites as can be observed in FIG. 3D. These additional experiments indicate that hemopressin behaves not just as an antagonist of $CB_1$ receptors but as an inverse agonist of $CB_1$ receptors similar to the highly selective synthetic compound rimonabant.

In addition to the aforementioned analysis, binding studies of the most important portions of the hemopressin amino acid sequence to the binding of $CB_1$ receptors were conducted. It was determined that the two phenylalanines of the hemopressin sequence should have characteristics of hydrophobic and aromatic groups and the leucine portion of the hemopressin sequence should have characteristics of a hydrophobic group. Hence, mimics, fragments or derivatives thereof with hydrophobic and aromatic groups at the phenylalanine region and hydrophobic groups at the leucine region were shown to bind most successfully with $CB_1$ receptors.

Additionally, in vivo studies were conducted demonstrating how hemopressin, its mimics, derivatives and fragments thereof, may be used to treat obesity. The results of these experiments concluded that hemopressin, its mimics, derivatives and fragments thereof, reduce fat content in rats without causing symptoms of depression. This is a significant improvement over the prior art because the prior art simply discusses a treatment using hemopressin to reduce food intake while this invention discloses a pharmaceutical composition containing hemopressin, a mimic, derivative or fragment thereof for the treatment of obesity by direct oxidation of fatty acids in blood plasma in muscles and the liver, without causing the common side effect of depression.

Experiments were conducted demonstrating that administration of hemopressin or its derivative HPW2, having the amino acid sequence PVNFK<u>W</u>LSH (SEQ ID NO:7), where tryptophan substitutes the C-terminal phenylalanine, to male Wistar rats that had been on an ad libitom 63-day diet once a day for three days resulted in a significantly reduced periepididymal and visceral fat content when compared to the control group that received just saline.

| Treatment | Body Weight (% of Control) | Periepididymal Adipose Tissue Weight (g) | Retroperitoneal Adipose Tissue Weight (g) | Visceral Adipose Tissue Weight (g) |
| --- | --- | --- | --- | --- |
| saline (n = 6) | 95.97 ± 8.20 | 5.66 ± 1.19 | 6.14 ± 1.56 | 3.72 ± 0.59 |
| hemopressin (HP) (n = 8) | 98.62 ± 13.33 | 4.77 ± 1.06 | 6.12 ± 2.09 | 2.77 ± 0.58 |
| HPW2 (n = 6) | 95.47 ± 15.44 | 4.01 ± 0.33 | 5.37 ± 1.11 | 2.63 ± 0.94 |

Experiments were also conducted on genetically obese and diet-induced rats of another species. Male Zucker rats were maintained on a 12 hour light/dark cycle. The rats were divided into two groups that receive once a day for three days either intraperiotoneal administration of 50 micrograms/Kg body weight of HPW2 or saline. After three days administration, intraperiotoneal administration of HPW2 resulted in significant reduction in retroperitoneal fat content.

Next, oral administration of hemopressin and HPW2 was demonstrated to significantly reduce the total body weight and periepididymal but not visceral fat content. Retroperitoneal fat content was significantly reduced by hemopressin only. Oral administration of rimonabant had similar effects on reducing fat content. Conversely, the oral administration of the non-cannabinoid peptide VDPENFRLLGNM (SEQ ID NO:9) had no effect on the rats' fat content.

| Treatment | Body Weight (% of Control) | Periepididymal Adipose Tissue Weight (g) | Retroperitoneal Adipose Tissue Weight (g) | Visceral Adipose Tissue Weight (g) |
|---|---|---|---|---|
| saline (n = 10) | 101.64 ± 0.60 | 9.70 ± 1.54 | 8.40 ± 1.75 | 4.38 ± 0.75 |
| hemopressin (HP) (n = 10) | 96.89 ± 1.25 | 7.16 ± 1.36 | 6.26 ± 1.62 | 4.31 ± 0.61 |
| HPW2 (n = 10) | 96.71 ± 2.03 | 7.32 ± 1.22 | 7.19 ± 1.50 | 4.28 ± 0.59 |
| rimonabant (n = 10) | 98.92 ± 0.95 | 5.57 ± 1.03 | 6.89 ± 1.31 | 3.91 ± 0.78 |
| non-cannabinoid peptide (n = 8) | 100.65 ± 8.07 | 9.38 ± 0.95 | 8.80 ± 1.15 | 4.81 ± 1.25 |

In order to ensure that hemopressin, its mimics, fragments or derivatives thereof would not have undesired side effects like rimonabant, studies were performed to help determine if hemopressin exists as a peptide in vivo. A spectrometric analysis was performed on the mass of rat brain fractions obtained by microwaves to minimize nonspecific post-mortem proteolyses. It was possible to identify from this experiment three new peptides containing hemopressin: VD PVNFKFLSH (SEQ ID NO:4), RVDPVNFKFLSH (SEQ ID NO:3), and RVDPVNFKFL (SEQ ID NO:10). The immunohistochemistry in rat brains suggested that hemopressin may also occur naturally in the neurons of distinct areas of rat brains. These additional studies demonstrated that peptides containing the hemopressin amino acid sequence are indeed generated in vivo. See FIG. 4A-J.

In fact, while rimonabant caused the expected depression of the animals during tests, animals receiving 1 mg/Kg hemopressin indeed showed no such symptoms as observed through a standard swimming test. See the results illustrated in FIG. 5.

Thus this invention demonstrates that hemopressin, its mimics, derivatives and fragments thereof, can effectively reduce fat content without causing depression in two distinctive animal models.

Finally, it has been demonstrated that administration of hemopressin, a mimic, derivative, or fragment thereof improves insulin sensitivity and may therefore be used for the prevention and treatment of diabetes.

It is generally understood that obese individuals have a higher propensity for suffering from diabetes. This disorder is characterized by high blood glucose in the context of insulin resistance and relative insulin deficiency. Insulin resistance is a physiological condition in which the natural hormone, insulin, becomes less effective in lowering blood sugars. The resulting increase in blood glucose may raise levels outside the normal range and cause adverse health effects. Certain cell types, particularly fat cells, require insulin to absorb glucose. When these cells fail to respond adequately to circulating insulin, blood glucose levels rise.

Insulin resistance in fat cells reduces the normal effects of insulin on lipids and results in reduced uptake of circulating lipids. Increased mobilization of stored lipids elevates free fatty acids in the blood plasma. Elevated blood fatty-acid concentrations contribute to elevated blood glucose levels.

Hemopressin, besides treating obesity, may therefore be used in the prophylactic treatment of diabetes by increasing insulin sensitivity thereby decreasing insulin resistance by oxidizing fatty acids in the blood plasma in muscles and the liver. This was demonstrated in an experiment on diet induced obese rats that were treated with a saline solution, 50 micrograms/Kg of hemopressin, HPW2, rimonabant, and 1 mg/Kg of hemopressin. Treatment of the diet induced obese rats with hemopressin significantly improved insulin sensitivity, as well as HPW2 derivative. Treatment with the synthetic antagonist rimonabant and the standard saline control solution did not produce similar results. See FIG. 6.

In conclusion, this invention demonstrates that the systemic or local administration of hemopressin, its mimics, derivatives or fragments thereof, make it a strong candidate for a new therapy for treating obesity by directly reducing body fat content, without the usual collateral effects of depression. Furthermore, the invention suggests that this treatment could also reduce the risk of diabetes and treat patients suffering from diabetes by increasing insulin sensitivity and effectively reducing blood glucose concentrations.

Although the present invention and its advantages have been described in detail, it must be understood that various changes, substitutions and alterations may be made without straying from the core and scope of the invention as defined in the claims appended hereto.

That which is claimed is:

1. A pharmaceutical composition for the treatment of obesity, comprising: hemopressin and a pharmaceutically acceptable vehicle, said pharmaceutical composition provides a reduction of body fat, and wherein the hemopressin is defined by amino acid sequence proline-valine-asparagine-phenylalanine-lysine-tryptophan-leucine-serine-histidine (SEQ ID NO:7).

2. The pharmaceutical composition according to claim 1, characterized in that said pharmaceutical composition may be administered intraperitoneally, intrathecally, or orally.

3. The pharmaceutical composition according to claim 1, characterized in that the hemopressin is administered in a dose varying from 0.05 micrograms per kilogram of body weight to 1 milligram per kilogram of body weight.

4. The pharmaceutical composition according to claim 3, characterized in that the hemopressin is administered in a dose varying from 0.05 micrograms per kilogram of body weight to 50 micrograms per kilogram of body weight.

5. The pharmaceutical composition as in claim 1, characterized in that the pharmaceutically acceptable vehicle is a sterile isosmotic solution with the same osmotic pressure of an isotonic solution of blood.

6. A pharmaceutical composition for treating diabetes, comprising: hemopressin and a pharmaceutically acceptable vehicle, said pharmaceutical composition improves insulin sensitivity, wherein the hemopressin is defined by amino acid sequence proline-valine-asparagine-phenylalanine-lysine-tryptophan-leucine-serine-histidine (SEQ ID NO:7).

7. The pharmaceutical composition according to claim 6, characterized in that said pharmaceutical composition may be administered intraperitoneally, intrathecally, or orally.

8. The pharmaceutical composition according to claim 6, characterized in that the hemopressin is administered in a dose varying from 0.05 micrograms per kilogram of body weight to 1 milligram per kilogram of body weight.

9. The pharmaceutical composition according to claim 8, characterized in that the hemopressin is administered in a dose varying from 0.05 micrograms per kilogram of body weight to 50 micrograms per kilogram of body weight.

10. The pharmaceutical composition as in claim 6, characterized in that the pharmaceutically acceptable vehicle is a sterile isosmotic solution with the same osmotic pressure of an isotonic solution of blood.

11. A method of treating a mammal suffering from obesity, comprising: administering the pharmaceutical composition of claim 1 to said mammal, wherein said mammal is suffering from obesity.

12. A method of treating a mammal suffering from diabetes, comprising: administering the pharmaceutical composition of claim 1 to said mammal, wherein said mammal is suffering from obesity.

* * * * *

SEQUENCE LISTING

```
<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
<223> OTHER INFORMATION: Synthesized

<400> SEQUENCE: 1

Asn Phe Lys Phe
1
```

<210> SEQ ID NO 2
<211> LENGTH: 9
<212> TYPE: PRT
<213> ORGANISM: Artificial Sequence
<220> FEATURE:
<223> OTHER INFORMATION: Synthesized

<400> SEQUENCE: 2

Pro Val Asn Phe Lys Leu Leu Ser His
1               5

<210> SEQ ID NO 3
<211> LENGTH: 12
<212> TYPE: PRT
<213> ORGANISM: Rattus sp.

<400> SEQUENCE: 3

Arg Val Asp Pro Val Asn Phe Lys Phe Leu Ser His
1               5                   10

<210> SEQ ID NO 4
<211> LENGTH: 11
<212> TYPE: PRT
<213> ORGANISM: Rattus sp.

<400> SEQUENCE: 4

Val Asp Pro Val Asn Phe Lys Phe Leu Ser His
1               5                   10

<210> SEQ ID NO 5
<211> LENGTH: 12
<212> TYPE: PRT
<213> ORGANISM: Homo sapiens

<400> SEQUENCE: 5

Arg Val Asp Pro Val Asn Phe Lys Leu Leu Ser His
1               5                   10

<210> SEQ ID NO 6
<211> LENGTH: 11
<212> TYPE: PRT
<213> ORGANISM: Homo sapiens

<400> SEQUENCE: 6

Val Asp Pro Val Asn Phe Lys Leu Leu Ser His
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthesized

<400> SEQUENCE: 7

Pro Val Asn Phe Lys Trp Leu Ser His
1               5

<210> SEQ ID NO 8
<211> LENGTH: 9
<212> TYPE: PRT
<213> ORGANISM: Rattus sp.

<400> SEQUENCE: 8

```
Pro Val Asn Phe Lys Phe Leu Ser His
1               5

<210> SEQ ID NO 9
<211> LENGTH: 12
<212> TYPE: PRT
<213> ORGANISM: Rattus sp.

<400> SEQUENCE: 9

Val Asp Pro Glu Asn Phe Arg Leu Leu Gly Asn Met
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthesized

<400> SEQUENCE: 10

Arg Val Asp Pro Val Asn Phe Lys Phe Leu
1               5                   10
```